(12) United States Patent
Hwang et al.

(10) Patent No.: US 9,753,027 B2
(45) Date of Patent: Sep. 5, 2017

(54) CANTILEVER SENSOR WITH SLIT AND BIOSENSOR HAVING THE SAME

(71) Applicant: KOREA INSTITUTE OF SCIENCE AND TECHNOLOGY, Seoul (KR)

(72) Inventors: Kyoseon Hwang, Seoul (KR); Tae Song Kim, Seoul (KR); Rhokyun Kwak, Seoul (KR); Won Woo Cho, Yongin-si (KR); Myung Sic Chae, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 14/575,129

(22) Filed: Dec. 18, 2014

(65) Prior Publication Data

US 2015/0253313 A1   Sep. 10, 2015

(30) Foreign Application Priority Data

Mar. 5, 2014  (KR) ........................ 10-2014-0025905

(51) Int. Cl.
| | | |
|---|---|---|
| *G01N 29/00* | (2006.01) | |
| *G01H 11/08* | (2006.01) | |
| *H01L 41/08* | (2006.01) | |
| *G01N 33/53* | (2006.01) | |
| *G01N 33/543* | (2006.01) | |

(Continued)

(52) U.S. Cl.
CPC ....... *G01N 33/5302* (2013.01); *G01N 29/022* (2013.01); *G01N 29/036* (2013.01); *G01N 33/5438* (2013.01); *G01N 33/54373* (2013.01); *G01N 2291/0427* (2013.01)

(58) Field of Classification Search
CPC ............. G01N 33/5302; G01N 2/0229; G01N 2291/0427
See application file for complete search history.

(56) References Cited

U.S. PATENT DOCUMENTS 5,633,552 A * 5/1997 Lee ................ A61B 17/320068
                                                          310/311
5,719,324 A   2/1998 Thundat et al.
(Continued)

FOREIGN PATENT DOCUMENTS

KR   WO 2010002056 A1 * 1/2010 ........... G01N 29/036

OTHER PUBLICATIONS

Ledermann, Nicolas, et al. "Piezoelectric Pb (Zrx, Ti1-x) O3 thin film cantilever and bridge acoustic sensors for miniaturized photoacoustic gas detectors." Journal of Micromechanics and Microengineering 14.12 (2004): 1650.*

(Continued)

*Primary Examiner* — Lyle Alexander
*Assistant Examiner* — Robert Eom
(74) *Attorney, Agent, or Firm* — NSIP Law

(57) ABSTRACT

The present disclosure relates to a cantilever sensor, and a biosensor having the same, wherein the cantilever sensor including a slit formed on a flat board and a cantilever formed by the slit, a first electrode formed on the cantilever, and a second electrode formed on the flat board countered to the first electrode about the slit, wherein the electrodes are formed on the cantilever sensor having the slit, whereby sensing can be conducted by an electric method, through which the sensor can be effectively miniaturized.

14 Claims, 19 Drawing Sheets

(51) Int. Cl.
*G01N 29/02* (2006.01)
*G01N 29/036* (2006.01)

(56) References Cited

U.S. PATENT DOCUMENTS

| | | | |
|---|---|---|---|
| 6,212,939 B1 | 4/2001 | Thundat | |
| 6,289,717 B1 | 9/2001 | Thundat et al. | |
| 7,288,873 B2* | 10/2007 | Salsman | H01Q 1/26 |
| | | | 310/322 |
| 2003/0054355 A1* | 3/2003 | Warthoe | C12Q 1/6825 |
| | | | 435/6.12 |
| 2006/0257286 A1* | 11/2006 | Adams | G01N 29/022 |
| | | | 422/82.01 |

OTHER PUBLICATIONS

Fritz et al., "Translating Biomolecular Recognition into Nanomechanics," Science, vol. 288, Apr. 14, 2000, pp. 316-318.
Wu et al., "Bioassay of prostate-specific antigen (PSA) using microcantilevers," Nature Biotechnology 19, 2001, pp. 856-860.
Park et al., "High-resolution cantilever biosensor resonating at air-liquid in a microchannel," Lab Chip, 2011, 11, pp. 4187-4193.

\* cited by examiner (a)

(b)

(c)

(d)

(a)

(b)

(c)

(d)

CANTILEVER SENSOR WITH SLIT AND BIOSENSOR HAVING THE SAME

Pursuant to 35 U.S.C. §119 (a), this application claims the benefit of earlier filing date and right of priority to Korean Patent Application No. 10-2014-0025905, filed on Mar. 5, 2014, the contents of which are hereby incorporated by reference in their entirety.

BACKGROUND OF THE DISCLOSURE

Field of the Disclosure

The present disclosure relates to a cantilever sensor, and more particularly to a cantilever sensor with a slit capable of sensing by way of an electric method through formation of an electrode on a cantilever sensor with a slit, through which a miniaturized cantilever sensor can be realized, and a biosensor having the same.

Discussion of the Related Art

The information disclosed in this Discussion of the Related Art section is only for enhancement of understanding of the general background of the present disclosure and should not be taken as an acknowledgement or any form of suggestion that this information forms the prior art already known to a person skilled in the art.

Recently, a miniaturized sensor fabricated by MEMS (Micro Electronic Mechanical System) process has become an object of interest, because the miniaturized sensor fabricated by MEMS process has a quicker response and higher sensitivity and is appropriate to mass production.

Most of the conventional cantilever sensors perform measurement by sensing resonance frequency variation or static deflection due to heat or mass variation using a light source such as laser.

As a measurement of static deflection of a cantilever sensor using an optical system, Nature Biotechnology 18, 856-860 (2001) and Science 288, 316-318 (2000) disclose a detection method of proteins and genes using biological reaction generated from surfaces of a micro cantilever.

The sensing method using static deflection is to determine whether there is a protein or a gene by concentration of laser to a sensing position diode through irradiation of a light source such as the laser to a cantilever surface. However, the method of measuring deformation of cantilever using a light source has a limitation in miniaturization and high integration due to requirement of a predetermined space for installation of optical system.

Furthermore, with regard to researches on micro cantilever sensor using resonance frequency variation, Cornell University reported possibility of detection of particular gas included in vacuum or air by a square cantilever, while Purdue University reported the possibility of detection of particular gas included in vacuum or air by manufacturing a miniaturized cantilever of about 3 μm length. In other examples, U.S. Pat. No. 5,719,324 discloses a cantilever sensor using reaction of chemical materials on a cantilever, particularly using resonance frequency variation for analysis of target chemical material. In other examples, U.S. Pat. Nos. 6,212,939 and 6,289,717 respectively disclose an invention on a chemical sensor by absorption in silicon cantilever, and an invention on a sensing sensor by coupling binding partner of material to be detected from a cantilever. However, the method of measuring the resonance frequency variation has disadvantage in that experimental error is great due to resonance frequency variation in response to viscosity variation of liquid sample, and sensitivity deteriorates due to damping of the cantilever on the liquid sample.

In a measure to overcome the aforementioned disadvantages, MIT attempted to allow the bio reaction to be realized within a cantilever structure by forming a micro-fluidic channel inside the cantilever structure to reduce the damping of the liquid sample, and Tokyo University attempted to increase the sensitivity by making a cantilever structure having a fine slit within several μm ranges as illustrated in FIGS. 1 and 2 (See Lab Chip, 2011 Dec. 21; 11(24):4187-93, Epub 2011 Oct. 28, High-resolution cantilever biosensor resonating at air-liquid in a micro-channel, Park J, Nishida S, Lambert P, Kawakatsu H, Fujita H.). However, the formation of micro-fluidic channel thus discussed has a disadvantage of complicating the cantilever structure, and the cantilever structure having a slit disadvantageously provides a difficulty in miniaturization due to use of laser light source.

SUMMARY OF THE DISCLOSURE

This section provides a general summary of the disclosure, and is not a comprehensive disclosure of its full scope or all of its features.

Exemplary aspects of the present disclosure are to substantially solve at least the above problems and/or disadvantages and to provide at least the advantages below. Accordingly, an aspect of the present disclosure provides a cantilever sensor with slit configured to enable a miniaturization of a sensor by sensing in an electric method, and a biosensor having the same.

It should be emphasized, however, that the present disclosure is not limited to a particular disclosure, as explained above. It should be understood that other technical subjects not mentioned herein may be appreciated by those skilled in the art.

In one general aspect of the present disclosure, there is provided a cantilever sensor with a slit, the cantilever sensor comprising:

a slit formed on a flat board and a cantilever formed by the slit;

a first electrode formed on the cantilever; and a second electrode formed on the flat board countered to the first electrode about the slit.

Preferably, but not necessarily, the slit may have a width within a range of 1 μm~20 μm.

Preferably, but not necessarily, the cantilever may include a fixed end connected to the flat board and a free end countered to the fixed end.

Preferably, but not necessarily, the first electrode may include a slit lengthily formed in a direction from the fixed end to the free end or in a direction from the free end to the fixed end.

Preferably, but not necessarily, the first electrode may touch at one end to a distal end of the free end.

Preferably, but not necessarily, the first electrode may include two or more electrodes, each electrode being distanced from the other electrode.

Preferably, but not necessarily, the two or more electrodes may be formed on a position axially symmetrically formed from the cantilever.

Preferably, but not necessarily, the second electrode may have a shape of covering a whole or a part of the first electrode.

Preferably, but not necessarily, the second electrode may include a portion countered to the free end of the cantilever and a portion countered to a circumference of the cantilever.

Preferably, but not necessarily, the cantilever sensor may further comprise a piezoelectric actuating layer formed around the cantilever.

Preferably, but not necessarily, the piezoelectric actuating layer may include a piezoelectric film, and upper and bottom electrodes each formed at an upper surface and a bottom surface of the piezoelectric actuating layer.

Preferably, but not necessarily, the piezoelectric actuating layer may have a width greater than that of the cantilever.

Preferably, but not necessarily, the piezoelectric actuating layer may be formed at a rear side of the fixed end of the cantilever.

Preferably, but not necessarily, the cantilever sensor may further comprise an electrode line formed between the piezoelectric actuating layer and the fixed end of the cantilever and connected to the first electrode.

In another general aspect of the present disclosure, there is provided a biosensor, the biosensor comprising a target material bonding material formed on a cantilever.

Preferably, but not necessarily, the biosensor may further comprise an Au thin film layer formed on an entire area or a partial area of the first electrode on the cantilever and bonded with the target material bonding material.

Preferably, but not necessarily, the biosensor may further comprise a channel configured to transfer a liquid sample included with a target material to one side of the cantilever.

In still another general aspect of the present disclosure, there is provided a method for manufacturing a cantilever sensor having a slit, the method comprising:

forming, on a flat board, a first electrode and a second electrode opposite to the first electrode; and manufacturing a cantilever by forming a slit between the formed first and second electrodes.

The above and other features of the present disclosure are discussed infra with reference to drawings and description in the Detailed Description.

Advantageous Effects

The present disclosure has an advantageous effect of teaching a cantilever sensor with slit to enable a sensing using an electric method, through which a miniaturized cantilever sensor can be realized.

BRIEF DESCRIPTION OF THE DRAWINGS

The above and other features of the present disclosure will now be described in detail with reference to certain exemplary embodiments thereof illustrated in the accompanying drawings which are given hereinafter by way of illustration only, and thus are not limitative of the present invention, and wherein.

Additional advantages, objects, and features of the disclosure will be set forth in part in the description which follows and in part will become apparent to those having ordinary skill in the art upon examination of the following or may be learned from practice of the disclosure. The objectives and other advantages of the disclosure may be realized and attained by the structure particularly pointed out in the written description and claims hereof as well as the appended drawings.

It is to be understood that both the foregoing general description and the following detailed description of the present disclosure are exemplary and explanatory and are intended to provide further explanation of the disclosure as claimed.

DETAILED DESCRIPTION

Various exemplary embodiments will be described more fully hereinafter with reference to the accompanying drawings, in which some exemplary embodiments are shown.

The present inventive concept may, however, be embodied in many different forms and should not be construed as limited to the example embodiments set forth herein. Rather, the described aspect is intended to embrace all such alterations, modifications, and variations that fall within the scope and novel idea of the present disclosure.

In describing the present disclosure, detailed descriptions of constructions, configuration, functions or processes well known in the art may be omitted to avoid obscuring appreciation of the present disclosure by a person of ordinary skill in the art with unnecessary detail regarding such known constructions and functions.

The terminology used herein is for the purpose of describing particular embodiments only and is not intended to be limiting of the general inventive concept. As used herein, the singular forms "a", "an" and "the" are intended to include the plural forms as well, unless the context clearly indicates otherwise.

The use of "including," "comprising," or "having" and variations thereof herein is meant to encompass the items listed thereafter and equivalents thereof as well as additional items. It will be understood that, although the terms first, second, etc. may be used herein to describe various elements, these elements should not be limited by these terms. These terms are only used to distinguish one element from another. For example, a first region/layer could be termed a second region/layer, and, similarly, a second region/layer could be termed a first region/layer without departing from the teachings of the disclosure.

1. Measuring Principle of Cantilever Having Slit

Figure 3:
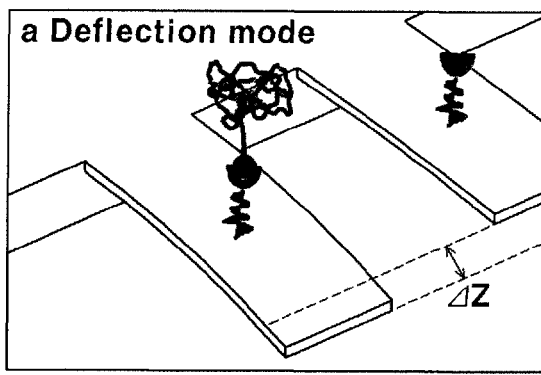
FIG. 3 is a mimetic diagram illustrating an example of measuring principle of a cantilever sensor according to the present disclosure.
Figure 3:
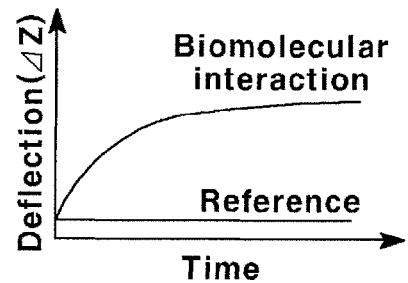
Figure 3:
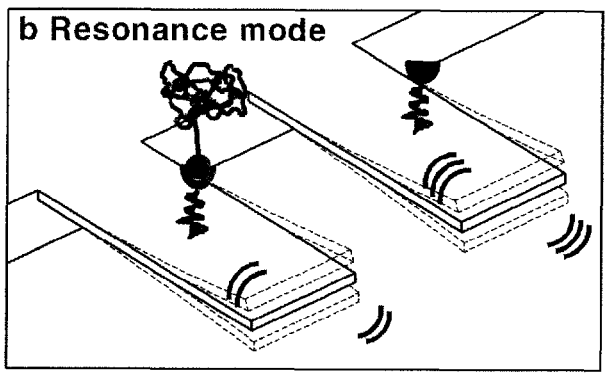
Figure 3:
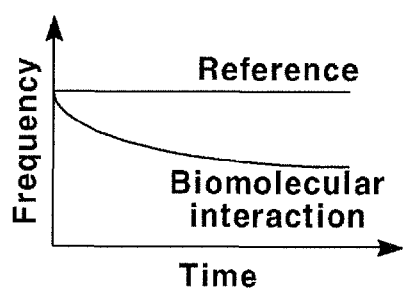

FIG. 3 is a mimetic diagram illustrating an example of measuring principle of a cantilever sensor according to the present disclosure.

Referring to FIG. 3, the principle of detecting a bio material using a micro cantilever may be divided to two types, that is, a static mode or deflection mode measuring deflection generated by surface stress variations when a particular bio reaction (e.g., antigen-antibody reaction) occurs on a surface of a micro cantilever sensor, and a dynamic mode measuring resonance frequency variations generated by changes in mass increase and spring constant. The resonance frequency which is a factor in measuring the dynamic mode may be defined by the following equation according to Hooke's law and Newton's second law:

$$f_0 = \frac{1}{2\pi}\sqrt{\frac{k}{m^*}}$$

where, $f_0$ is resonance frequency, $m^*$ is a cantilever mass, k is a spring constant. When a receptor (e.g., antibody) fixed on the surface of a cantilever and a to-be-detected target material (e.g., antigen) are coupled, the mass of the cantilever increases due to addition of the mass of the target material. Furthermore, the cantilever is generated with a compressive stress due to repulsive force being applied to the target material, because the target material has the same electric charge as neighboring organic molecules, whereby the spring constant decreases to resultantly reduce the resonance frequency. The quantitative analysis of bio material can be performed by measuring resonance frequency variations of the micro cantilever sensor using the abovementioned dynamic mode.

Figure 4:
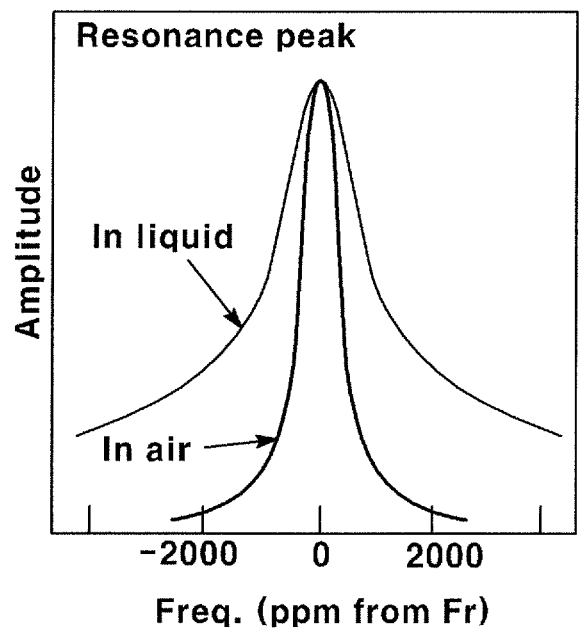
FIG. 4 is a graph illustrating a decreasing aspect of q-factor which is a sensitivity value when a cantilever sensor is positioned in a liquid.
Figure 5:
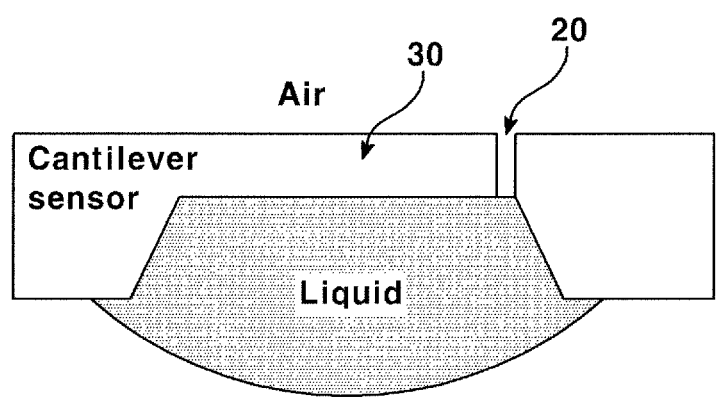
FIG. 5 is a conceptual view illustrating an example of a cantilever sensor having a slit in order to increase a q-factor value according to the present disclosure.

FIG. 4 is a graph illustrating a decreasing aspect of q-factor which is a sensitivity value when a cantilever sensor is positioned in a liquid, and FIG. 5 is a conceptual view illustrating an example of a cantilever sensor having a slit in order to increase a q-factor value according to the present disclosure.

When bio material is to be detected using a micro cantilever sensor, because a bio material-existent environment is liquid, and when a cantilever sensor without slit is positioned inside liquid, the cantilever sensor shows a tendency where a signal is reduced by damping of the liquid, which is a same principle as that of more energy being consumed when walking in a swimming pool than walking on a flat ground. In view of resonance frequency measurement, when a cantilever sensor without slit is driven inside liquid, a resonance frequency measurement signal is horizontally spread as shown in FIG. 4 {which is called 'quality (q)-factor decreased'}, where sensor sensitivity decreases due to hindrance of accurate resonance frequency measurement.

In order to minimize the sensitivity decrease due to reduction in q-factor under environment inside the liquid, a slit wrapping a circumference of cantilever sensor is basically formed at a micrometer level in the present disclosure, and liquid including sample is positioned only at one side (upper surface or bottom surface) of the cantilever sensor for use. The micrometer-level slit cannot pass through the liquid, such that when the liquid is positioned only at one surface of the cantilever sensor, the liquid is relatively reduced in damping over a case where the liquid is located both on and under the cantilever sensor, whereby q-factor can be improved to increase the sensitivity.

2. Detailed Example of Cantilever Having Slit

Figure 6:
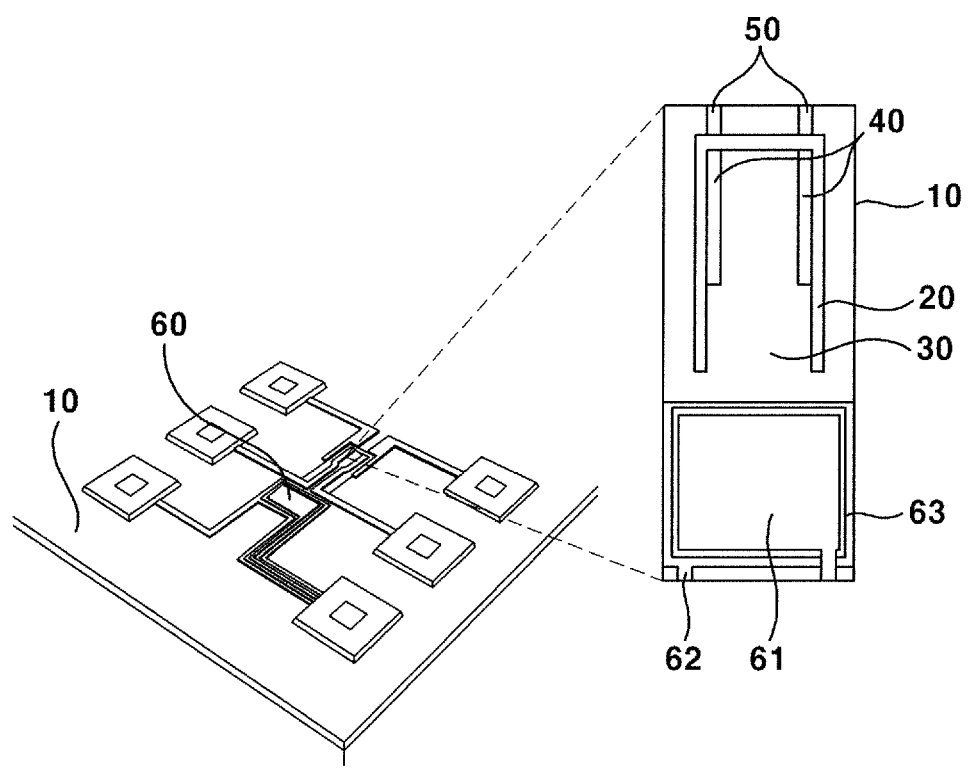
FIG. 6 is a detailed view illustrating a detailed configuration of a cantilever sensor according to an exemplary embodiment of the present disclosure.
Figure 7:
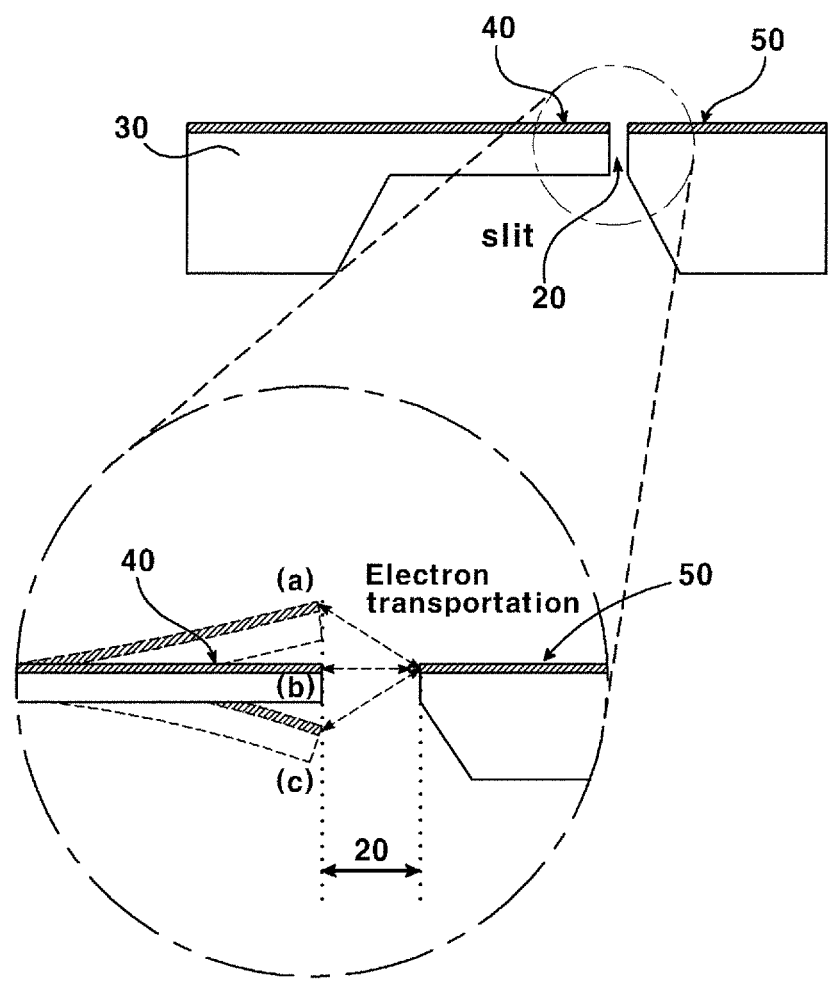
FIG. 7 is a conceptual view illustrating an example of size of a signal received in response to movement of a cantilever sensor according to the present disclosure.

FIG. 6 is a detailed view illustrating a detailed configuration of a cantilever sensor according to an exemplary embodiment of the present disclosure, and FIG. 7 is a conceptual view illustrating an example of size of a signal received in response to movement of a cantilever according to the present disclosure.

Referring to FIG. 6, the cantilever sensor according to an exemplary embodiment of the present disclosure may include a cantilever (30) formed by a slit (30), a first electrode (40) and a second electrode (50). The cantilever (30) is manufactured by the slit (20) formed on a flat board (10), and a sensor according to the present disclosure may include the slit (20) formed on the flat board (10) as a separate element. The cantilever (30) may include any structure where one distal end thereto is fixed while the other distal end is freely movable, and may usually take a shape of rectangular board, but the present disclosure is not limited thereto, and the cantilever may take a triangular shape, an oval shape or other shapes.

For example, the cantilever (30) may include a fixed end (31) connected to a flat board and a free end (32) countered to the fixed end (31). The cantilever (30) may be manufactured using a substrate formed with silicon, and may further include a separate plate material using silicon nitride and/or silicon oxide. The cantilever is particularly limited in size but preferably has a length of 10 μm~1,000 μm and a width of 5 μm~500 μm for detection of fine matters.

The cantilever (30) according to the present disclosure may be simultaneously manufactured by forming the slit (20) on the flat board (20). That is, an external shape of the cantilever (30) can be formed by punching the flat board (10) using the slit (20). For example, as illustrated in FIG. 6, when a "⊏" shaped slit (20) is formed on the flat board (20), an interior of the slit (20) becomes the cantilever (30). The flat board (10) may be a board formed with silicon, and methods for forming the slit (20) are not particularly limited. The slit (20) prevents liquid including a sample from passing through but reduces a damping phenomenon generated by the liquid, and the slit according to the present disclosure is a gap in which electrons can move between the first electrode (40) and the second electrode (50) (described later). To this end, width of the slit (20) may be in the range of 1 μm~20 μm, preferably in the range of 3 μm~15 μm, and more preferably in the range of 5 μm~10 μm. When the width is less than the abovementioned ranges, the movement of the cantilever is disadvantageously obstructed to prevent a smooth movement of electrons, whereby a signal value may become smaller, and when the width is more than the abovementioned ranges, the disadvantage is that q-factor value may become smaller or the liquefied sample may pass the slit.

The first electrode (40) is formed on the cantilever (30), and characteristically moves along with the movement of the cantilever (30). The first electrode (40) may be formed on entire surface or a partial surface of the cantilever (30), and the number, shape or direction of the first electrode (40) is not particularly limited.

The second electrode (50) is formed on the flat board (10) countered to the first electrode (40) about the slit (20). That is, the second electrode (50) formed on the flat board (10) is formed to communicate with the first electrode (40) formed on the cantilever (30). In other words, the second electrode (50) is a base electrode configured to receive a signal transmitted from the first electrode (40) in response to the movement of the cantilever (30). In order to transmit a signal between the first and second electrodes (40, 50), it is preferable that the first and second electrodes (40, 50) be symmetrically formed at mutually facing positions. That is, the first and second electrodes (40, 50) are characteristically formed at a symmetrical or opposite position with the slit (20) positioned therebetween, whereby it is possible to electrically measure a resonance frequency of the cantilever (30).

For example, as illustrated in FIG. 7, signal strength transmitted through a micro slip can be measured after a DC voltage is applied to two communication electrodes, i.e., the first and second electrodes (40, 50), positioned at one surface of the cantilever. Thus, real time measurement of signal strength transmitted through the communication electrodes can learn a frequency when displacement is the greatest {(a) and (c) of FIG. 7} and a frequency when the displacement is the smallest {(b) of FIG. 7}. A distance between the two electrodes (40, 50) is the longest when the displacement is the largest, and an electrical energy movement is the minimum, and a distance is the shortest when the displacement is the smallest and an electrical energy movement is the maximum. In this method, the resonance frequency of the cantilever can be accurately measured.

As noted from the foregoing, the present disclosure teaches that a signal is transmitted between the first and second electrodes (40, 50) with the first electrode (40) formed at the cantilever (30) and the slit (20) positioned therebetween, and although the number, shape, size and/or position of the first and second electrodes (40, 50) may be different, it would be preferable that these are mutually same or similar.

Furthermore, when the first electrode (40) is lengthily formed from the fixed end (31) to the free end (32) on the cantilever, or the first electrode (40) is lengthily formed from the free end (32) to the fixed end (31) on the cantilever, the movement of cantilever (30) can be well reflected, whereby signal can be advantageously transmitted with more accuracy and greater strength. Furthermore, when a distal end of the first electrode (40) is in touch with a distal end of the free end (32) of the cantilever (30), movement of electrons with the second electrode (50) can be further smoothed to obtain an effect of greater signal change.

Thus, one of the characteristics in the present disclosure is to arrange mutually opposing communication electrodes on the cantilever (30) sensor having slit, whereby sensing is enabled using an electric method to allow achieving an effect of miniaturizing the sensor. The present disclosure may further include a piezoelectric actuating layer (60) formed around the cantilever (30) as another characteristic.

The piezoelectric actuating layer (60) is arranged around the cantilever (30) and transmits a vibration signal to the cantilever (30) whereby amplitude of signals generated from between mutually opposing electrodes, i.e., first electrode (40) and the second electrode (50), can be greatly increased. The piezoelectric actuating layer (60) includes a piezoelectric film or a piezoelectric membrane configured to generate a vibration. For example, the piezoelectric actuating layer (60) may include a piezoelectric film (63) and upper/bottom electrodes (61, 62) to which an AC signal having a low frequency wave and an AC signal having a high frequency wave are alternately applied to transmit a vibration energy to the cantilever (30). Furthermore, a DC voltage can be applied to the first and second electrodes (40, 50) to measure the magnitude of a voltage signal transmitted through the slit (20).

Thus, the cantilever (30) vertically vibrates with a greatest displacement when an AC signal with a same frequency as that of the cantilever (30) is transmitted through the piezoelectric film (63), whereby the magnitude of the signal transmitted through the first and second electrodes (40, 50) can be measured in real time to learn a frequency when the displacement is the greatest, and this method enables a more accurate measurement of the resonant frequency of the micro cantilever (30).

At this time, when the piezoelectric actuating layer (60) has a width greater than that of the cantilever (30), the cantilever (30) can be more effectively transmitted with more vibration energy. Furthermore, although the piezoelectric actuating layer (60) may be formed at any place about the cantilever (30), formation of the piezoelectric actuating layer (60) at a rear side (anchor part) of the fixed end (31) enables a more effective transmission of vibration energy to the cantilever (30). At this time, the rear side (anchor part) means a concept including a portion where the cantilever (30) is connected and supported to a flat plate, and/or a portion of a direction opposite to the free end (32) from the fixed end (31).

Furthermore, the present disclosure further comprises an electrode line (41) connected to the first electrode (40), where the electrode line (41) is preferably formed between the piezoelectric actuating layer (60) and the cantilever (30), or between the piezoelectric actuating layer (60) and the fixed end (31) of the cantilever (30). The arrangement of the electrode line (41) between the piezoelectric actuating layer (60) and the cantilever (30) can arrange the piezoelectric actuating layer (60) closer to the cantilever (30) and further enable integration and miniaturization of the sensor.

Figure 8:
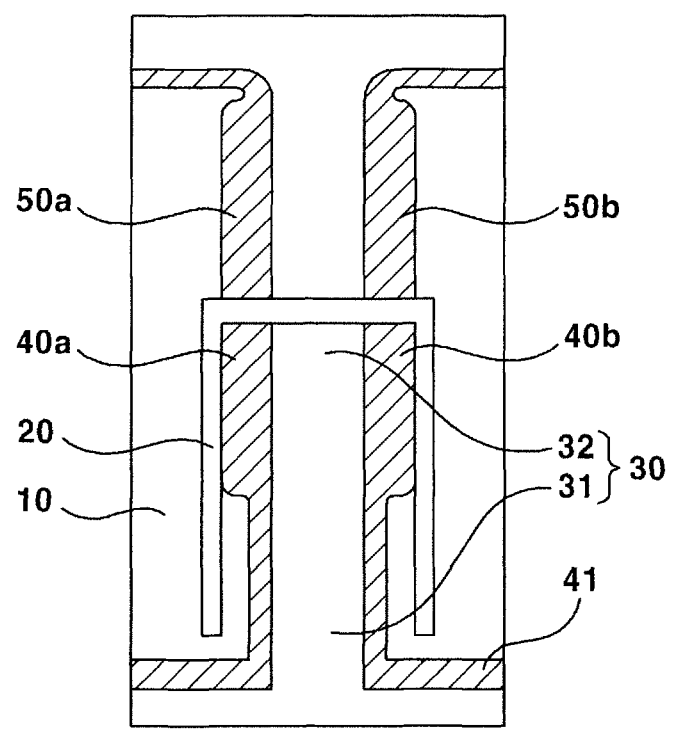
FIG. 8 is a partially enlarged view illustrating an example of 'A' type first and second electrodes of a cantilever sensor according to the present disclosure.
Figure 9:
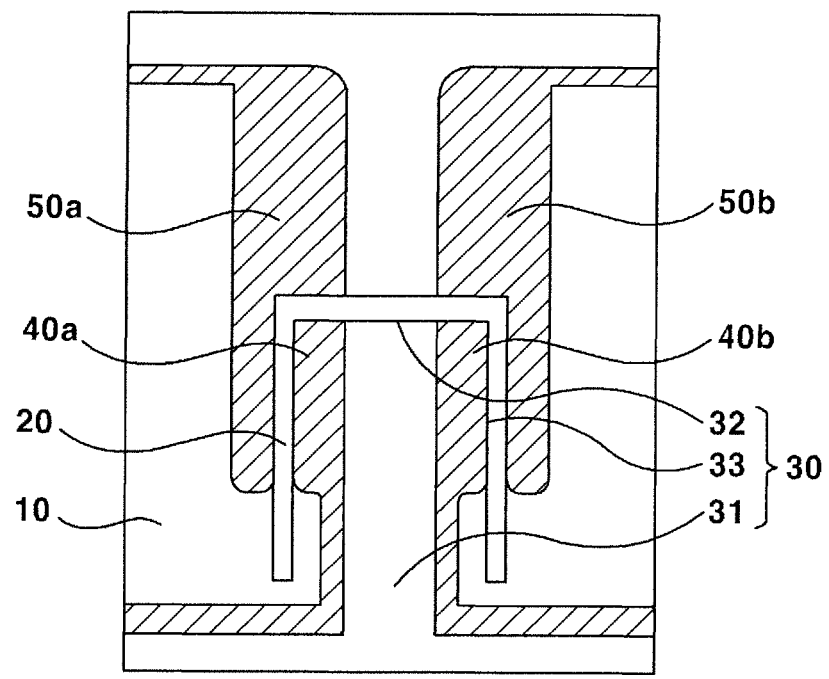
FIG. 9 is a partial enlarged view illustrating an example of 'B' type first and second electrodes of a cantilever sensor according to the present disclosure.

FIG. 8 is a partially enlarged view illustrating an example of 'A' type first and second electrodes of a cantilever sensor according to the present disclosure, and FIG. 9 is a partial enlarged view illustrating an example of 'B' type first and second electrodes of a cantilever sensor according to the present disclosure.

First, although the first electrode (40) according to the present disclosure is formed in one unit, it may be possible to include two or more electrodes (40a, 40b), each one spaced apart from the other. Furthermore, although the second electrode (50) according to the present disclosure is formed in one unit, it may be also possible to include two or more electrodes (50*a*, 50*b*), each one spaced apart from the other. The micro level cantilever (30) may be horizontally uneven, and when two or more electrodes are used as mentioned above instead of using one electrode, a signal can be effectively detected from both sides in a balanced manner. To this end, it is preferable that two more electrodes be respectively positioned at both lateral ends on one surface of the cantilever (30), and it is more preferable that the two more electrodes be formed at point-symmetrical positions or axially-symmetrical positions from the center of the cantilever.

Furthermore, as illustrated in FIG. 9, the second electrode (50) is preferably formed with a shape to wrap a whole portion or a partial portion of the first electrode (40). That is, the second electrode (50) may be formed by continuously including a portion facing the free end (31) of the cantilever (30) and a portion facing a periphery (33) of the cantilever (30). When the second electrode (50) has a shape as mentioned above, the second electrode (50) has an effect of receiving a signal from or transmitting the signal to the first electrode (40) without any omission.

Meantime, in another general aspect of the present disclosure, there is further provided a biosensor, the biosensor comprising a target material bonding material formed on the cantilever (30).

The target material bonding material, which is to capture a target material that is an object to be analyzed or detected, may vary depending on the target material, and the target material and a bonding material for the target material may include all materials known to the technical field.

Figure 18:
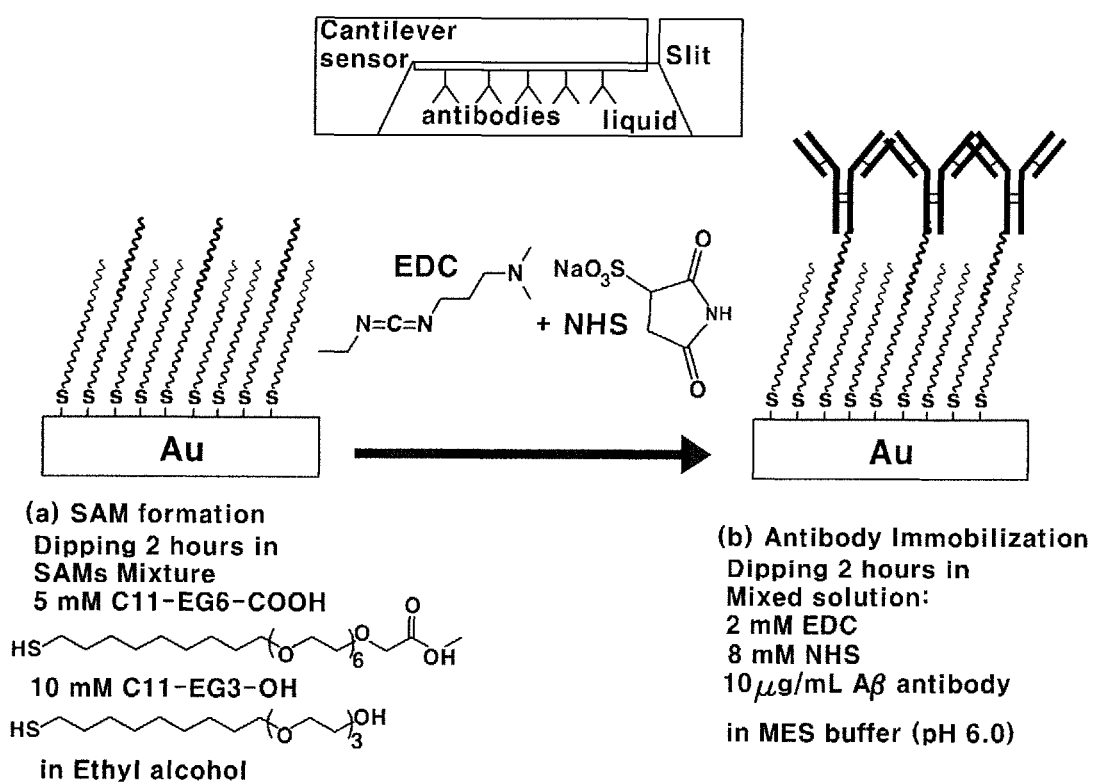
FIG. 18 is a conceptual view illustrating an example of a method for coupling a target material bonding material to a cantilever sensor according to the present disclosure.

Furthermore, the biosensor may be formed on the cantilever (30) or on an entire area or a partial area of the first electrode (40), and may further include an Au thin film layer bonded by the target material bonding material (See FIG. 18). The Au thin film layer may be formed on the cantilever (30) or the first electrode (40) to facilitate easy bond of the target material bonding material, and may include all widgets known in the technical field.

Figure 1:
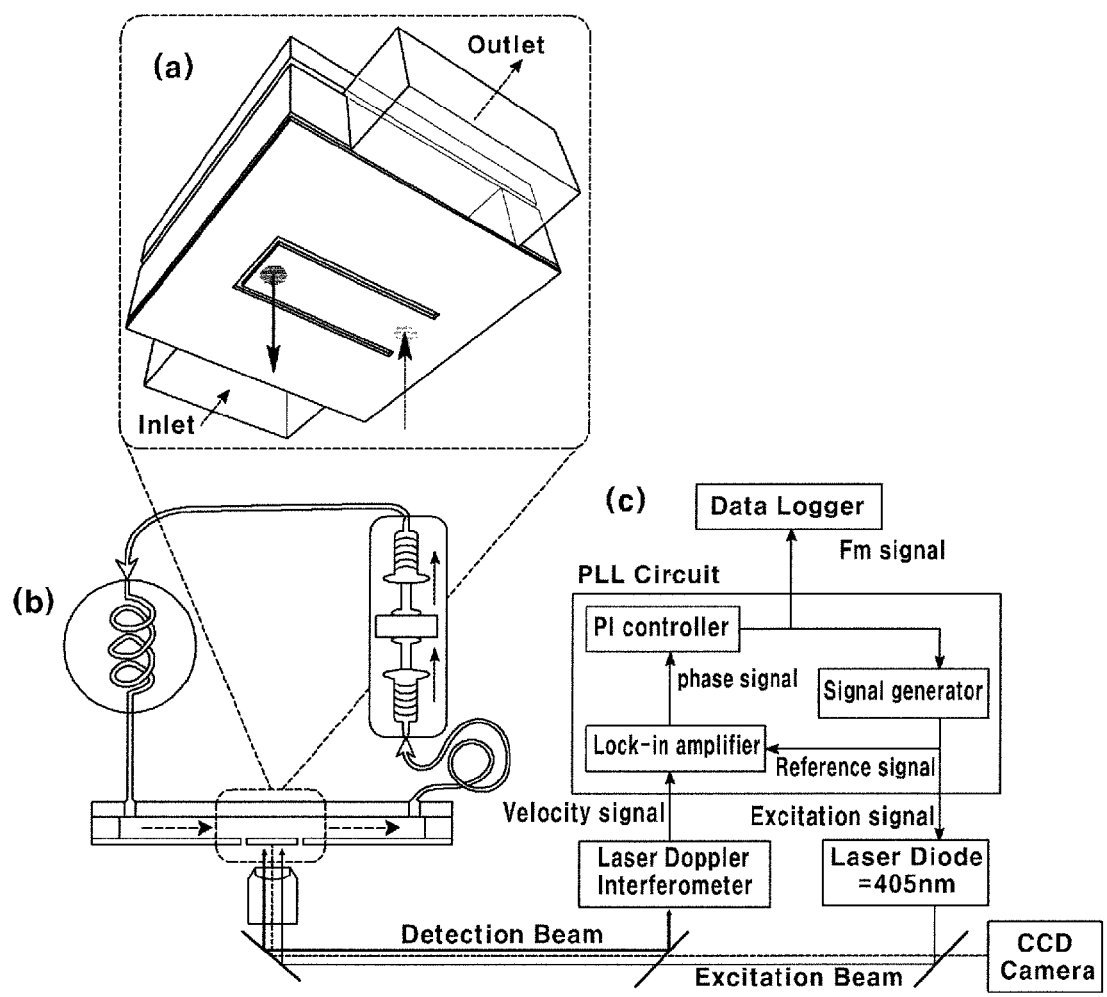
FIG. 1 includes a perspective view (a) illustrating a structure of a cantilever sensor, a parts coupling view (b) and a flowchart (c) according to prior art.
Figure 2:
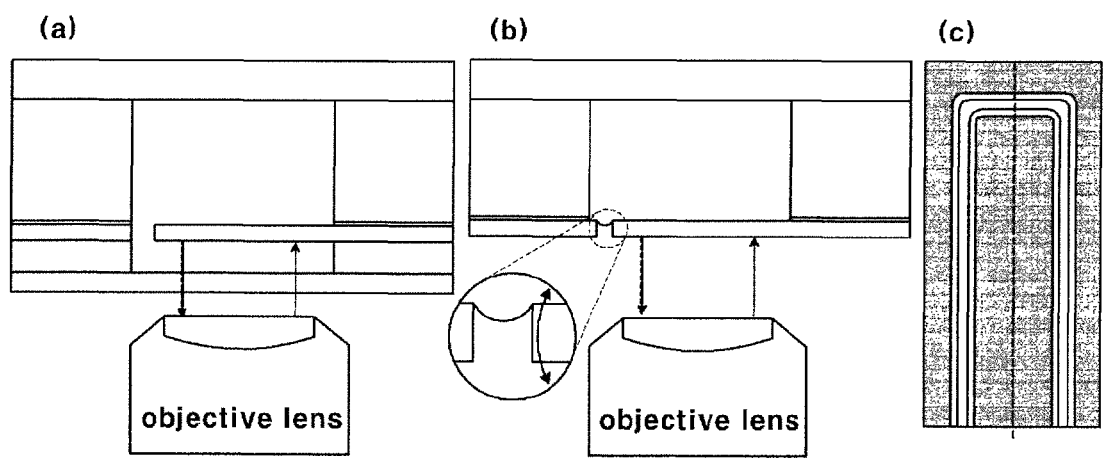
FIG. 2 includes cross-sectional views (a, b) and a slip photograph (c) illustrating a laser optical method of a cantilever sensor of FIG. 1.

The biosensor may further comprise a channel (not shown) configured to transfer a liquid sample included with a target material to one side of the cantilever (30) (See FIGS. 1 and 2). The channel may be arranged at an upper surface or a bottom surface of the cantilever (30), and it is more preferable that the channel be formed to a direction perpendicular to a lengthwise direction of the cantilever (30), because movement of cantilever (30) is prevented from being hindered by movement of samples.

Figure 10:
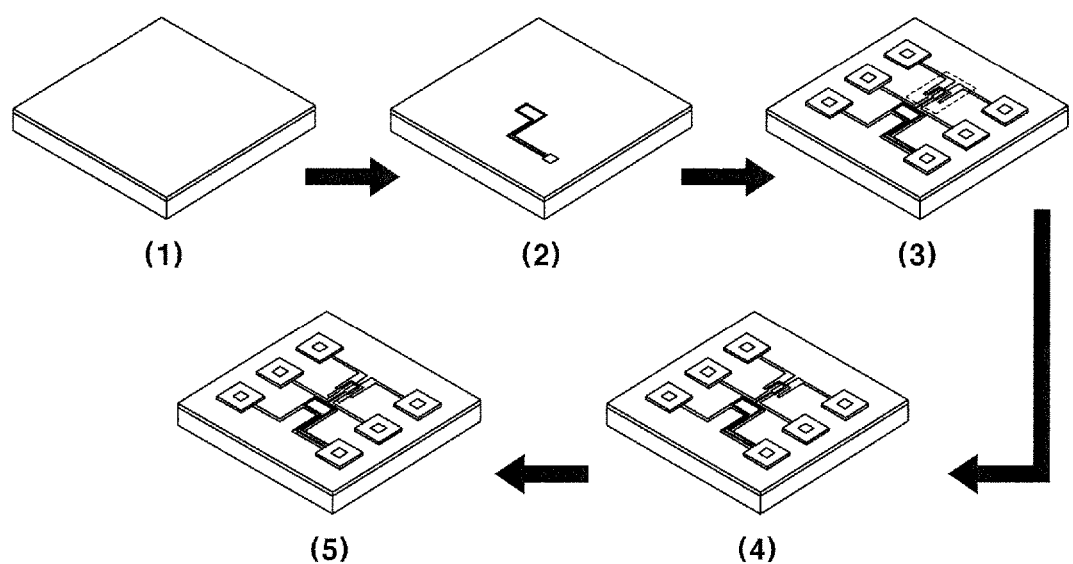
FIG. 10 is a flowchart illustrating a method for manufacturing a cantilever sensor according to an exemplary embodiment of the present disclosure.

FIG. 10 is a flowchart illustrating a method for manufacturing a cantilever sensor according to an exemplary embodiment of the present disclosure.

The method for manufacturing a cantilever sensor having a slit according to an exemplary embodiment of the present disclosure may comprise: forming, on a flat board (10), a first electrode (40) and a second electrode (50) opposite to the first electrode (40) (S100); and manufacturing a cantilever (30) by forming a slit (20) between the formed first and second electrodes (40, 50) (S200).

The basic characteristic in the cantilever (30) having a slit (20) according to the present disclosure is to form the first electrode (40) and the second electrode (50) opposite to the first electrode (40) about the slit (20), and particularly, to form a slit after depositing the first electrode (40) and the second electrode (50) on the flat board (10). The method for manufacturing a cantilever sensor having a slit according to an exemplary embodiment of the present disclosure has an advantageous effect of solving the problem where the pastes for forming electrodes are filled in several µm levels of slits (20).

To be more specific, the step (S100) of forming the first electrode (40) and the second electrode (50) may include a multi-layer deposition process {FIG. 10(1)}, an actuating layer and communication electrode patterning process {FIG. 10(2)}, a passivation and Au pad patterning process {FIG. 10(3)}, and an Si bulk etching process {FIG. 10(4)}.

The multi-layer deposition process (S110) includes depositing a silicon nitride film on at least one surface of a substrate formed with silicon and the like, and stacking materials for forming the piezoelectric actuating layer and the first and second electrodes. For example, Pt/PZT/Pt may be sequentially deposited for forming a bottom electrode, a piezoelectric membrane and an upper electrode of the piezoelectric actuating layer, and the bottom Pt may be used for forming the first and second electrodes {FIG. 10(1)}.

The actuating layer and communication electrode patterning process (S120) includes forming the piezoelectric actuating layer and the first and second electrodes by sequentially etching the multi-layered deposited layers from the top. For example, the upper Pt layer is etched to form an upper electrode of the piezoelectric actuating layer, the PZT layer is etched to form a piezoelectric membrane, and the bottom Pt layer is etched to form a bottom electrode of the piezoelectric actuating layer. In separate or concurrent process thereabove, the bottom Pt layer may be etched from a position different from that of the piezoelectric actuating layer to form the first and second electrodes according to the present disclosure {See FIG. 10(2)}.

Figure 11:
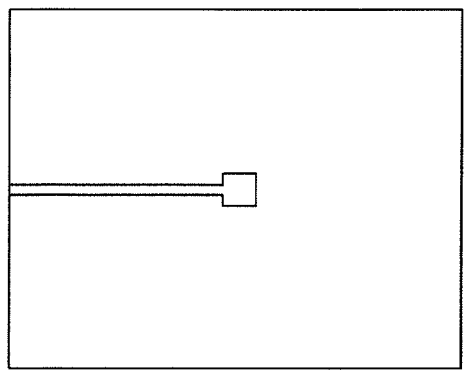
FIG. 11 is a photograph illustrating an example of a cantilever sensor that has gone through a multi-layer deposition process, an actuating layer and communication electrode patterning process according to the present disclosure.
Figure 11:
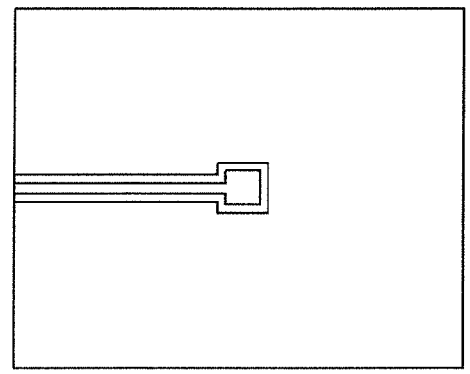
Figure 11:
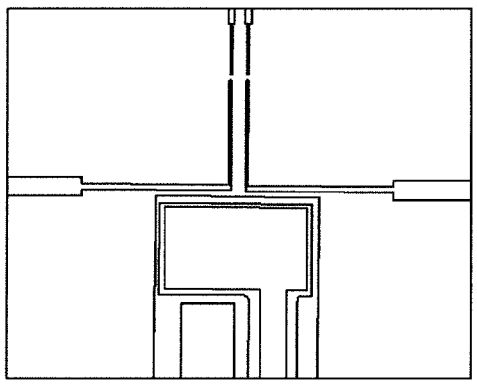
Figure 11:
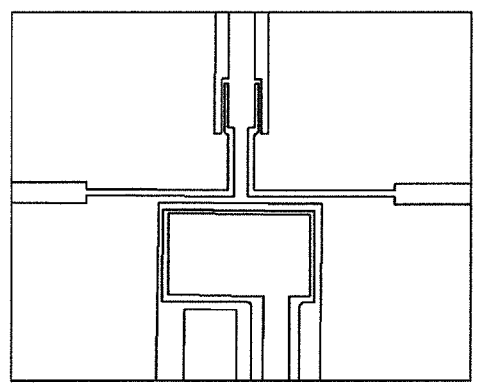

FIG. 11 is a photograph illustrating an example of a cantilever sensor that has gone through the multi-layer deposition process (S110), and the actuating layer and communication electrode patterning process (S120) according to the present disclosure, where FIG. 11(*a*) illustrates a state in which an upper electrode of a piezoelectric actuating layer is formed by etching the upper Pt layer, and a lower left photo of FIG. 11(*b*) illustrates a state where a piezoelectric membrane is formed by etching the PZT layer, FIG. 11(*c*) illustrates an example of cantilever sensor that has gone through the multi-layer deposition process (S110), and the actuating layer and communication electrode patterning process (S120) according to the present disclosure in order to form the first and second electrodes of cantilever sensor in A type, and FIG. 11(*d*) illustrates an example of cantilever sensor that has gone through the multi-layer deposition process (S110), and the actuating layer and communication electrode patterning process (S120) according to the present disclosure in order to form the first and second electrodes of cantilever sensor in B type.

Furthermore, the passivation and Au pad patterning process (S130) includes depositing a silicon nitride film as a protective layer, and forming an electrode connection terminal. For example, a protective layer may be formed by evenly depositing $SiO_2$ on an entire surface of a sensor having gone through the actuating layer and communication electrode patterning process (S120), which is to protect the sensor from solutions in which chemical materials and ions are dissolved when the cantilever sensor is performed with a surface treatment later. The passivation and Au pad patterning process (S130) may further include a Pt electrode contact hole etching process in which the silicon nitride film {which is an insulation material deposited on parts (a part the target material bonding material and/or a distal end of the free end of the first electrode)} of the first and second electrodes for later fixing the target material bonding material to the first electrode of the cantilever and for signal transmission of the first and second electrodes. Then, flow proceeds to the Au pad patterning process, which is to facilitate contact of all electrodes necessary for providing and measuring a signal by being connected from the cantilever to the outside {See FIG. 10(3)}.

Figure 12:
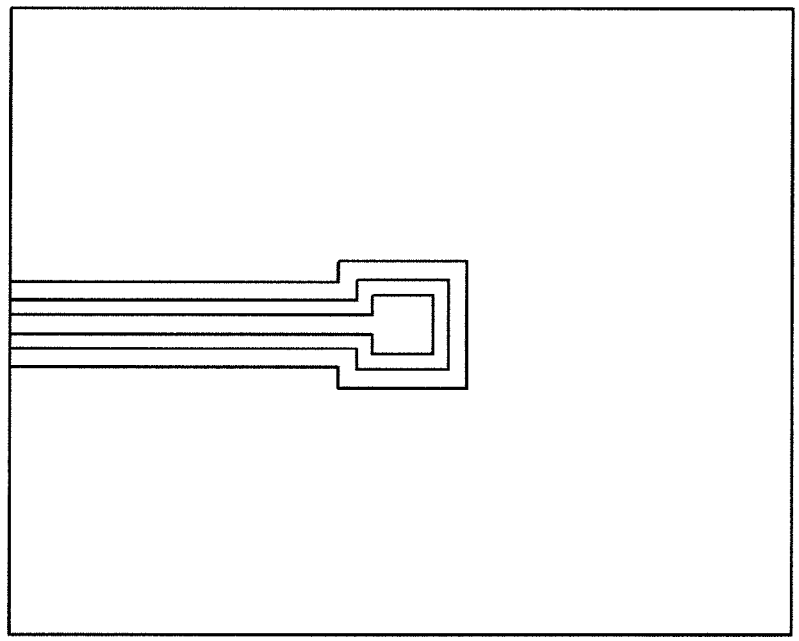
FIG. 12 is a photograph illustrating an example of a cantilever sensor that has gone through a passivation process and Au pad patterning process according to the present disclosure.
Figure 12:
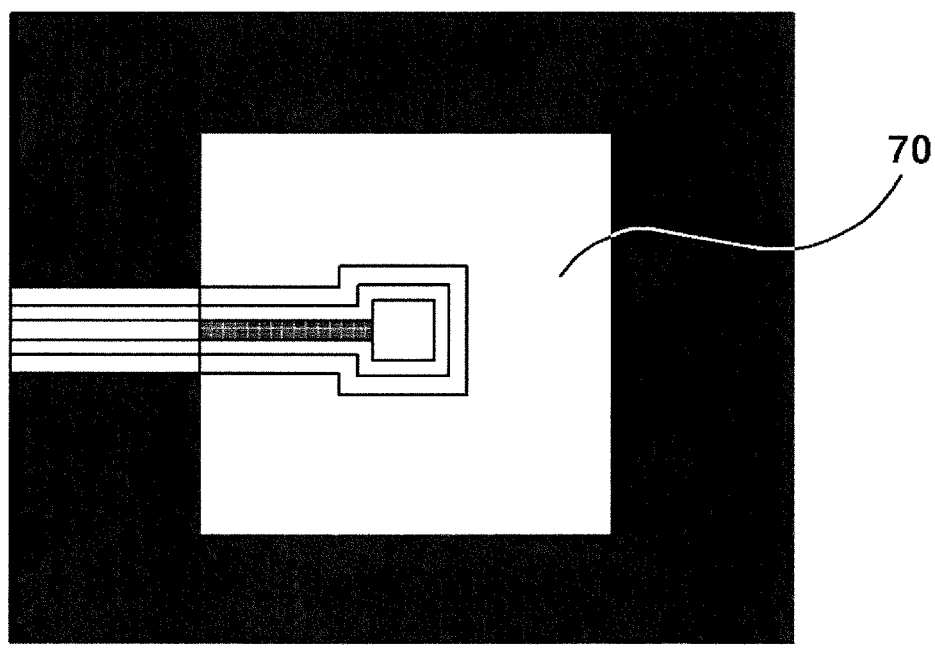

FIG. 12 is a photograph illustrating an example of a cantilever sensor that has gone through the passivation process and Au pad patterning process (S130) according to the present disclosure, where an Au terminal is illustrated in a shape of a rectangular pad.

Successively, the Si bulk etching process (S140) includes etching only the part of a rear surface of the sensor having gone through the abovementioned processes that is formed with the cantilever to reduce the thickness of the cantilever to a thinner thickness. For example, a bottom surface SiNx/Si including a part to be formed with the cantilever at a bottom surface of the sensor having gone through the S130 process and a part including a part of second electrode is etched to form a part to be formed with the cantilever using SiNx/SiO$_2$ {See FIG. 10(4)}.

Figure 13:
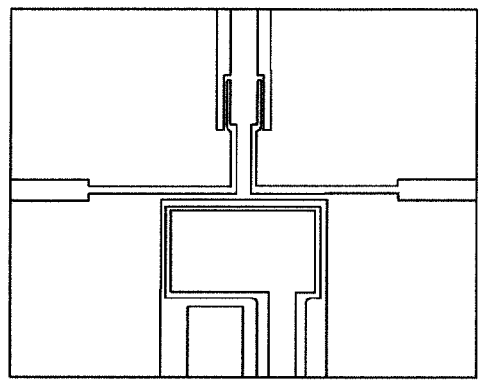
FIG. 13 is a photograph illustrating an example of a cantilever sensor that has gone through a Si bulk etching process and a slit patterning process according to the present disclosure.
Figure 13:
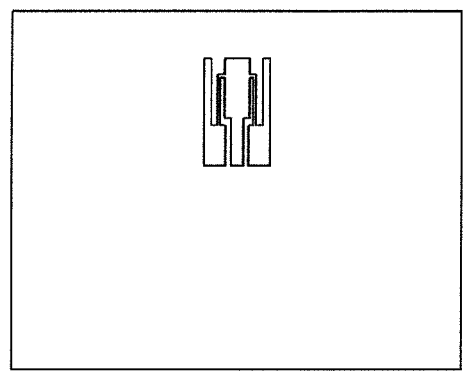
Figure 13:
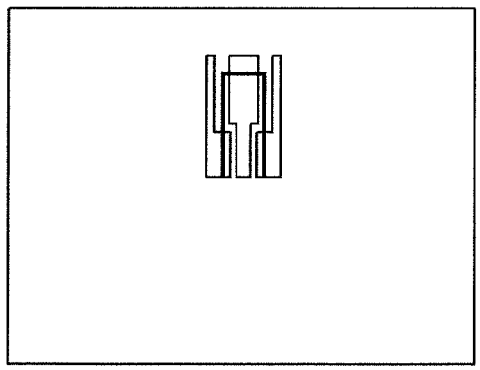
Figure 13:
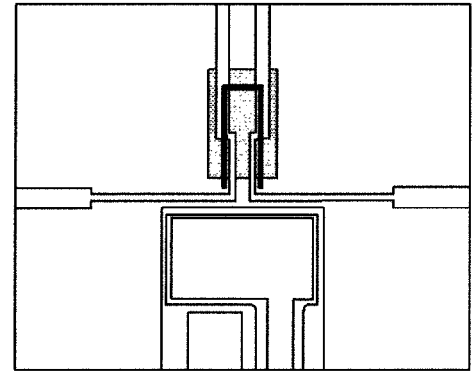

A left photo of FIG. 13 illustrates an example of a cantilever sensor that has gone through the Si bulk etching process (S140), and particularly, a portion etched through the etching process can be ascertained as illustrated in FIG. 13(*b*). FIG. 13(*a*) illustrates an example of cantilever sensor having gone through the Si bulk etching process (S140) in order to form the first and second electrodes of the cantilever sensor according to the present disclosure in A type. FIG. 13(*d*) illustrates an example of cantilever sensor having gone through the Si bulk etching process (S140) in order to form the first and second electrodes of the cantilever sensor according to the present disclosure in B type.

Successively, a step (S200) manufacturing the cantilever (30) by forming the slit (20) may include a slit patterning process {S210, FIG. 10(5)}. The slit patterning process (S210) is to form a slit at a predetermined position for manufacturing the cantilever (30). For example, a slit is formed at a position between where first and second electrodes are formed to allow the first electrode to face the second electrode across the slit {FIG. 10(5)}. A right photo of FIG. 13 shows an example of the cantilever having gone through the slit patterning process (S210), whereby it can be ascertained that a slit is formed between the first and second electrodes.

The present disclosure may be better understood by the following exemplary embodiments, and the following exemplary embodiments are provided only for exemplary purposes and not for limiting the protection scope limited by the enclosed claims.

2. Exemplary Embodiments: Manufacturing of Cantilever Sensor

The micro cantilever sensor was manufactured using an MEMS (Micro Electro Mechanical System) engineering process.

First, both sides of 4" silicon wafer were deposited with SiNx of 1 μm thickness using LPCVD (Low Pressure Chemical Vapor Deposition) method, and the wafer was deposited thereon with a platinum layer of bottom electrode with a 0.15 μm thickness using sputtering method. A PZT film of 2 μm thickness which is a piezoelectric film providing a vibration energy to the cantilever sensor was deposited on the platinum film using sol-gel method, and the PZT film was deposited with platinum of 0.1 μm thickness as an upper electrode using sputtering method.

Thereafter, the wafer deposited with multi-layered film was sequentially etched from the top layer. A piezoelectric actuating layer was manufactured by etching the upper platinum, PZT, and bottom electrode platinum film and simultaneously a communication electrode was manufactured by etching the bottom electrode platinum film.

Successively, an entire surface is deposited with silicon oxidation film of 0.2 μm thickness using the PECVD (Plasma Enhanced Chemical Deposition) method. At the same time, an Au contact electrode is formed using a lift-off method to manufacture an electrode for signal processing. Thereafter, the silicon is bulk-etched to adjust the thickness of the micro cantilever to approximately 1.2 μm thickness. Successively, the slit is patterned and etched to manufacture the micro cantilever sensor including a slit and a piezoelectric film.

Figure 14:
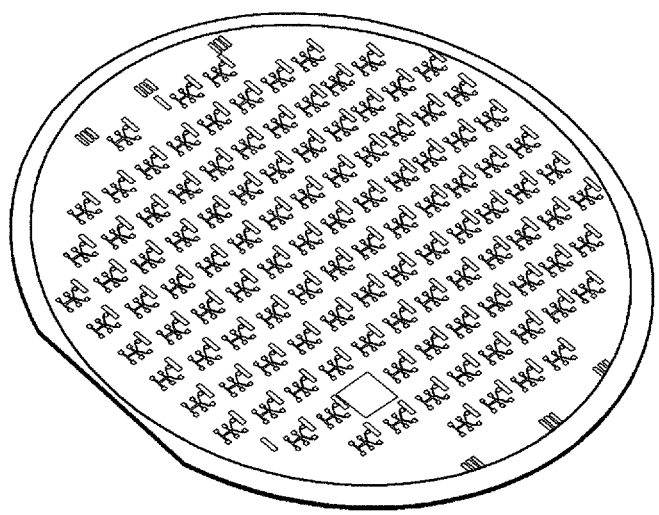
FIG. 14 is a photograph illustrating an example of a plurality of cantilever sensors formed on a wafer according to the present disclosure.
Figure 15:
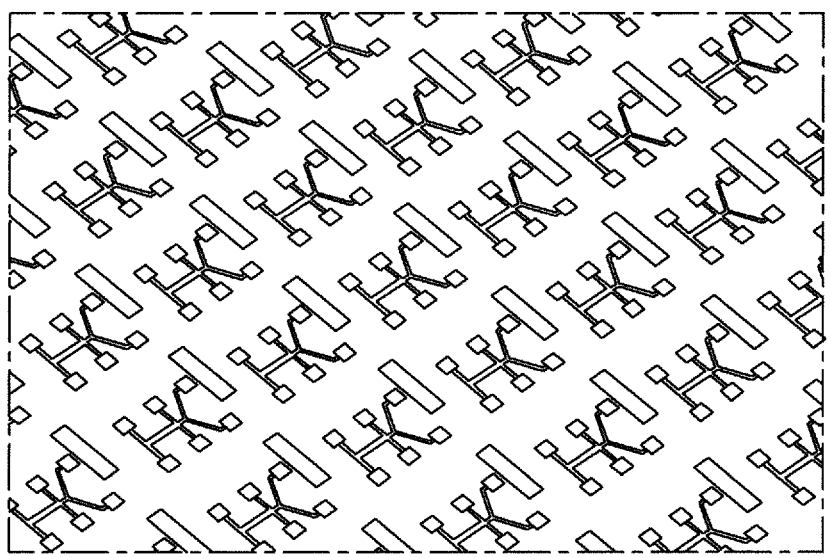
FIG. 15 is a partially enlarged view of FIG. 14.
Figure 16:
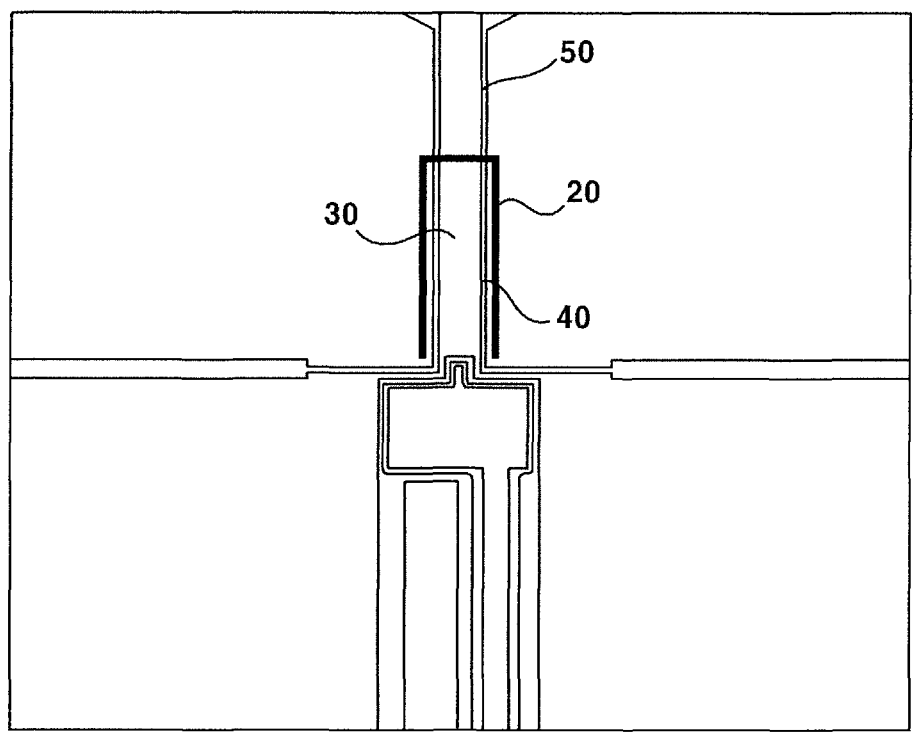
FIG. 16 is an enlarged view illustrating an example of an 'A' type cantilever sensor manufactured according to the present disclosure.
Figure 17:
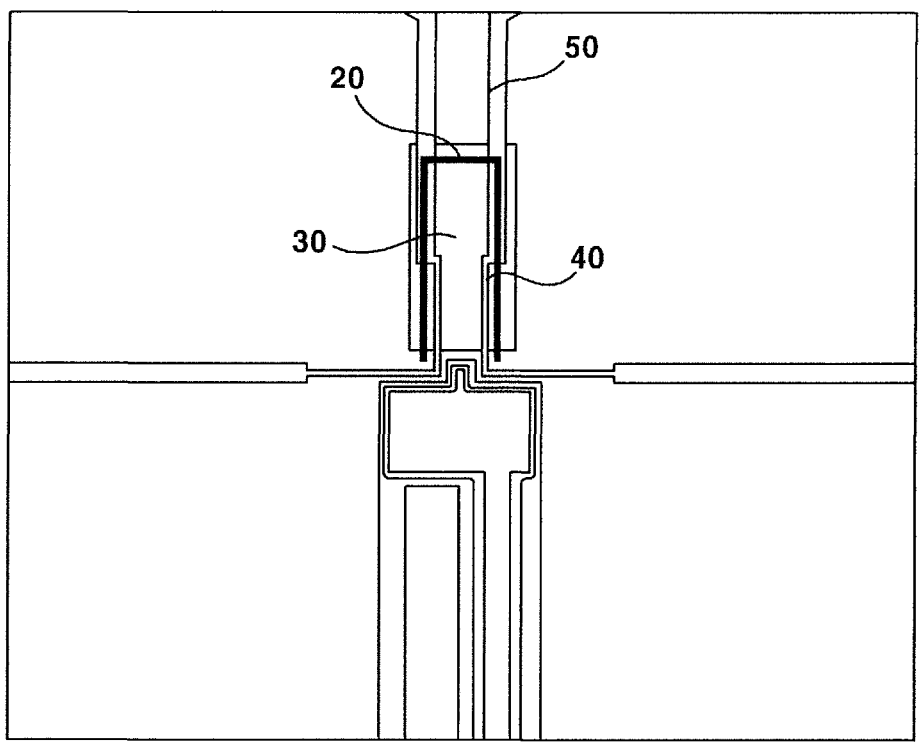
FIG. 17 is an enlarged photograph illustrating an example of a 'B' type cantilever sensor according to the present disclosure.

FIG. 14 is a photograph illustrating an example of a plurality of cantilever sensors formed on a wafer according to the present disclosure, FIG. 15 is a partially enlarged view of FIG. 14, FIG. 16 is an enlarged view illustrating an example of an 'A' type cantilever sensor manufactured according to the present disclosure, and FIG. 17 is an enlarged photograph illustrating an example of a 'B' type cantilever sensor according to the present disclosure.

3. Experimental Examples: Experiments to Detect Biomaterials

An attempt was made to detect a specific biomaterial inside the liquid using the micro cantilever sensor manufactured by the abovementioned exemplary embodiments. To this end, an Au film was deposited on an upper surface or a bottom surface of the micro cantilever.

FIG. 18 is a conceptual view illustrating an example of a method for coupling a target material bonding material to a cantilever sensor according to the present disclosure. As illustrated in FIG. 18, the deposited Au film is formed with an ethylene glycol-based SAM (Self Assembled Monolayer), on which a beta (β)-amyloid antibody for diagnosing the Alzheimer's disease was fixed.

Figure 19:
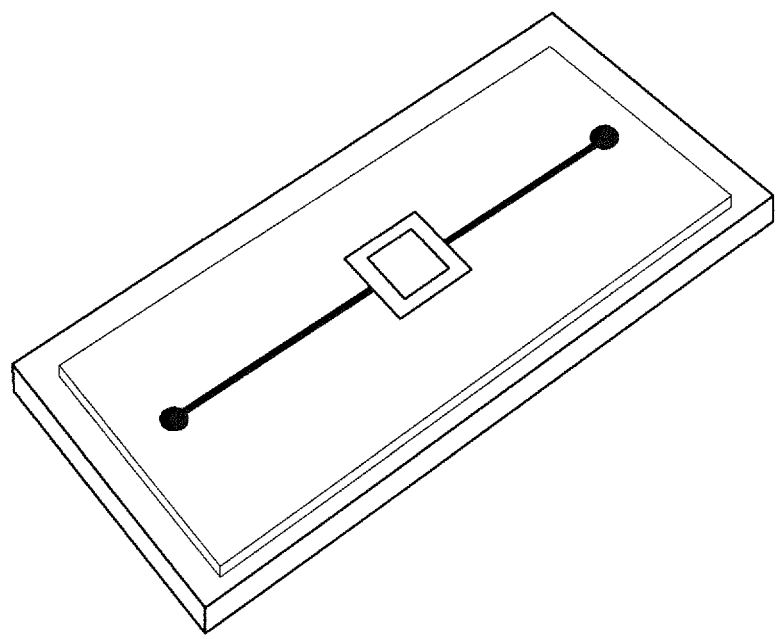
FIG. 19 is a photograph illustrating an example of a bio sensor including a sample transportation channel according to the present disclosure.

FIG. 19 is a photograph illustrating an example of a bio sensor including a sample transportation channel according to the present disclosure. Referring to FIG. 19, the micro cantilever sensor fixed with the beta-amyloid antibody was positioned at a chip formed with a channel for injecting the liquid, and a resonant frequency was measured by connecting the electrodes of the sensor to a measurement unit.

Figure 20:
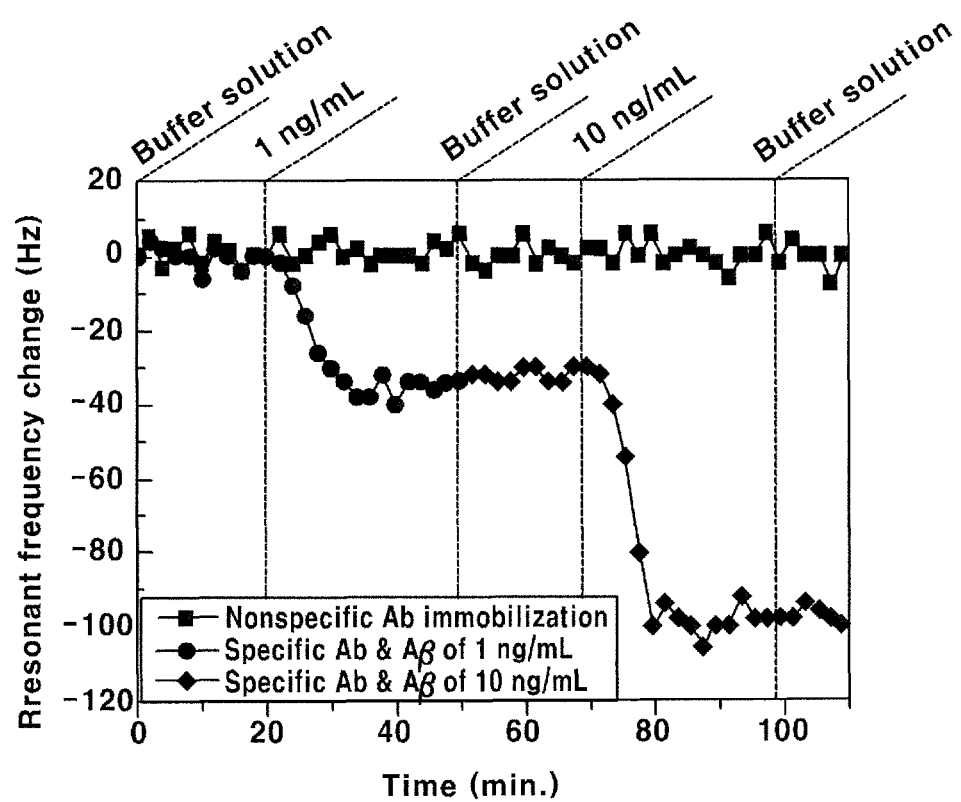
FIG. 20 is a graph illustrating an example of a result that has detected β-amyloid using a biosensor according to the present disclosure.

FIG. 20 is a graph illustrating an example of a result that has detected beta (β)-amyloid using a biosensor according to the present disclosure.

As illustrated in FIG. 20, a PBS (Phosphate buffered saline) buffer solution was injected into the chip mounted with the micro cantilever sensor to measure the resonant frequency for about 20 minutes, and then, solution dissolved with beta (β)-amyloid to be detected was injected. At this time, concentration of the injected solution was 1 ng/m L, and the resonant frequency was continuously decreased by about 38 Hz by bond between the antibody and the beta (β)-amyloid after the injection of solution. After reaching a saturation level (about 20 minutes after the injection of beta (β)-amyloid solution), and the buffer solution was re-injected and an attempt was made to remove non-specific absorbed protein by measuring the resonant frequency. Thereafter, beta (β)-amyloid solution of 10 ng/mL was injected again to observe a changed magnitude of resonant frequency. It was observed that the resonance frequency had been greatly reduced after injection and a saturated state was reached after reduction by about 60 Hz, whereby a possibility of detecting the biomaterial using the change in resonant frequency of the micro cantilever sensor including the slit and the piezoelectric film was ascertained.

Furthermore, it was ascertained that biomaterial of about 1 ng/mL level inside the liquid can be detected as a result of application of the micro cantilever sensor to the detection of biomaterial.

Figure 21:
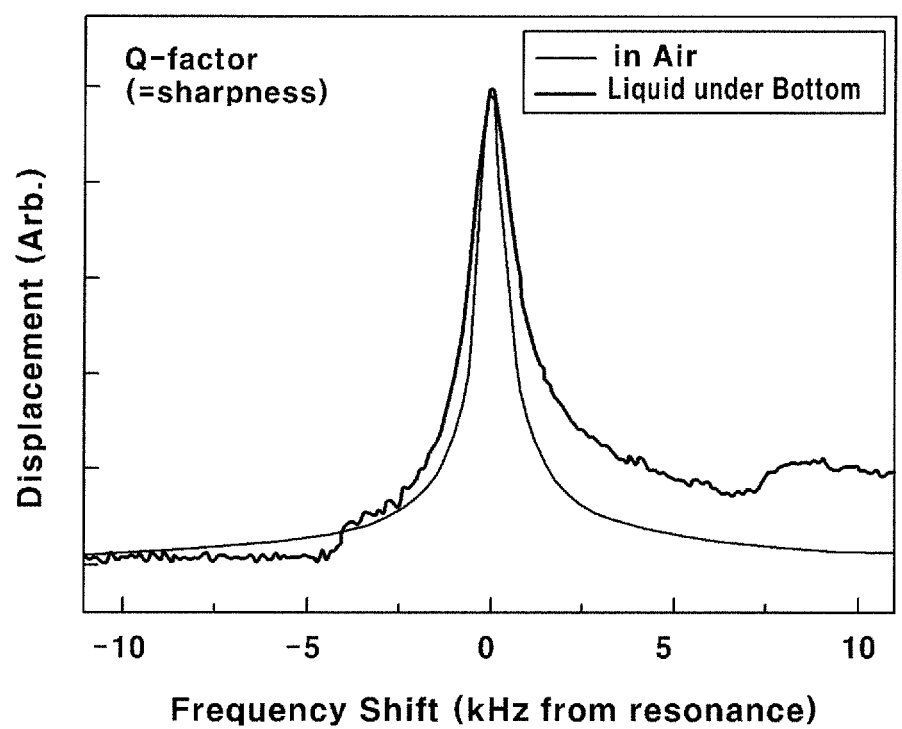
FIG. 21 is a graph illustrating an example of a resonance frequency analysis result in the air and in the liquid sample using a biosensor according to the present disclosure.

FIG. 21 is a graph illustrating an example of a resonance frequency analysis result in the air and in the liquid sample using a biosensor according to the present disclosure.

As illustrated in FIG. 21, although the q-factor of the micro cantilever sensor according to the present disclosure decreased a bit over a level (about 100) in air when the liquid was injected, it was ascertained that the micro cantilever sensor according to the present disclosure has an excellent q-factor (20~40) by as much as 10 times at the maximum over the q-factor (2~4) of the micro cantilever sensor positioned in the liquid according to prior art. The q-factor thus mentioned can be asserted to have shown that the sensitivity impediment had been minimized in measuring a biomaterial at trace level existing in the liquid.

The q-factor can be generally defined as $$Q\text{-factor} = \frac{Fr}{\delta Fr_{3dB}},$$

where Fr is a resonant frequency, and delta $Fr_{3\,dB}$ is a difference of frequencies when a total of two frequencies, each having about 0.707 in value, and existing at left and right of the resonant frequency when an amplitude (y axis) of the resonant frequency is viewed as 1.

For example, the q-factor value decreases, when the delta $Fr_{3\,dB}$ value increases as a resonant shape in the liquid is greatly broadened.

For example, in case of a cantilever sensor with width and length respectively at 30 and 90 μm according to the present disclosure, and when a liquid sample is positioned at one side of the cantilever sensor, the resonant frequency is about 80 kHz, and the delta $Fr_{3\,dB}$ is about 2.1 kHz, whereby it can be known that the cantilever sensor has about 38 q-factors by 80,000/2,100.

The above-mentioned cantilever sensor with a slit and biosensor having the same according to the present disclosure may, however, be embodied in many different forms and should not be construed as limited to the embodiments set forth herein. Thus, it is intended that embodiments of the present disclosure may cover the modifications and variations of this disclosure provided they come within the scope of the appended claims and their equivalents.

While particular features or aspects may have been disclosed with respect to several embodiments, such features or aspects may be selectively combined with one or more other features and/or aspects of other embodiments as may be desired.

What is claimed is:

1. A cantilever sensor, the cantilever sensor comprising:
a flat board comprising
a cantilever portion, the cantilever portion comprising a free end and a fixed end connected to a remaining portion of the flat board, and
a slit formed in the flat board, wherein the slit is disposed around a perimeter of the cantilever portion, and a width of the slit from a perimeter of the cantilever portion to the remaining portion of the flat board is constant;
a first electrode pair formed on the cantilever portion, wherein the first electrode pair comprises
two electrodes formed, in a length-wise direction, along the cantilever portion from the fixed end of the cantilever portion to the free end of the cantilever portion, and
each of the two electrodes is formed on a same surface of the cantilever portion; and
a second electrode pair, wherein each electrode of the second electrode pair is formed on the remaining portion of the flat board opposite from each electrode of the first electrode pair, respectively.

2. The cantilever sensor of claim 1, wherein the electrodes of the first electrode pair are formed on a position axially symmetrical to the cantilever portion.

3. The cantilever sensor of claim 1, wherein the second electrode pair has a shape in contact with the slit and is formed opposite at least one surface of the first electrode pair.

4. The cantilever sensor of claim 1, wherein the second electrode pair includes a portion disposed on the opposite side of the slit from the free end of the cantilever portion, and another portion otherwise disposed on the opposite side of the slit from a length-wise segment of the cantilever portion.

5. The cantilever sensor of claim 1, further comprising:
a piezoelectric actuating layer formed around the cantilever portion.

6. The cantilever sensor of claim 5, wherein the piezoelectric actuating layer includes: a piezoelectric film, and upper and bottom electrodes formed respectively at an upper surface and a bottom surface of the piezoelectric actuating layer.

7. The cantilever sensor of claim 5, wherein the piezoelectric actuating layer has a width greater than that of the cantilever portion.

8. The cantilever sensor of claim 5, wherein the piezoelectric actuating layer is formed at an adjacent side of the fixed end of the cantilever portion.

9. The cantilever sensor of claim 8, further comprising:
an electrode line formed between the piezoelectric actuating layer and the fixed end of the cantilever portion, and connected to the first electrode pair.

10. The cantilever sensor of claim 1, wherein the two electrodes of the first electrode pair are formed parallel to each other on opposite sides of the cantilever portion.

11. A biosensor comprising:
a flat board comprising
a cantilever portion, the cantilever portion comprising a free end and a fixed end connected to a remaining portion of the flat board, and
a slit formed in the flat board, wherein the slit is disposed around a perimeter of the cantilever portion, and a width of the slit from a perimeter of the cantilever portion to the remaining portion of the flat board is constant;
a first electrode pair formed on the cantilever portion, wherein the first electrode pair comprises
two electrodes formed, in a length-wise direction, along the cantilever portion from the fixed end of the cantilever portion to the free end of the cantilever portion, and
each of the two electrodes is formed on a same surface of the cantilever portion; and
a second electrode pair, wherein each electrode of the second electrode pair is formed on the remaining portion of the flat board opposite from each electrode of the first electrode pair, respectively; and a target material bonding material formed on the cantilever portion.

12. The biosensor of claim 11, further comprising:
a gold (Au) thin film layer formed on an entire area, or a partial area, of the first electrode fair on the cantilever portion, and bonded with the target material bonding material.

13. The biosensor of claim 11, further comprising:
a channel configured to transfer a liquid sample included with a target material to one side of the cantilever portion.

14. The biosensor of claim 11, wherein the two electrodes of the first electrode pair are formed parallel to each other on opposite sides of the cantilever portion.

* * * * *